(12) United States Patent
Von Wallfeld et al.

(10) Patent No.: US 11,786,994 B2
(45) Date of Patent: Oct. 17, 2023

(54) METHOD FOR PRODUCING A TRANSMISSIVE OPTICS

(71) Applicant: Aixlens GmbH, Alsdorf (DE)

(72) Inventors: Axel Von Wallfeld, Herzogenrath (DE); Reinhart Poprawe, Aachen (DE); Christian Fornaroli, Aachen (DE); Edgar Willenborg, Wuerselen (DE); Christian Weingarten, Aachen (DE); Uwe Clasen, Aachen (DE)

(73) Assignee: AIXLENS GMBH, Alsdorf (DE)

( * ) Notice: Subject to any disclaimer, the term of this patent is extended or adjusted under 35 U.S.C. 154(b) by 877 days.

(21) Appl. No.: 16/468,397

(22) PCT Filed: Oct. 12, 2017

(86) PCT No.: PCT/DE2017/000337
§ 371 (c)(1),
(2) Date: Jun. 11, 2019

(87) PCT Pub. No.: WO2018/108192
PCT Pub. Date: Jun. 21, 2018

(65) Prior Publication Data
US 2021/0260842 A1 Aug. 26, 2021

(30) Foreign Application Priority Data

Dec. 13, 2016 (DE) ..................... 10 2016 014 747.4
Mar. 28, 2017 (DE) ..................... 10 2017 002 986.5

(51) Int. Cl.
*B29D 11/00* (2006.01)
*B23K 26/0622* (2014.01)
(Continued)

(52) U.S. Cl.
CPC ............ *B23K 26/36* (2013.01); *A61F 2/1618* (2013.01); *B22F 10/66* (2021.01); *B23K 26/034* (2013.01);
(Continued)

(58) Field of Classification Search
CPC ........ B29D 11/00451; B29D 11/00951; B29D 11/023; B23K 26/0624; B23K 26/082;
(Continued)

(56) References Cited

U.S. PATENT DOCUMENTS

| | | |
|---|---|---|
| 5,143,660 A | 9/1992 | Hamilton et al. |
| 6,043,452 A | 3/2000 | Bestenlehrer |

(Continued)

FOREIGN PATENT DOCUMENTS

| | | |
|---|---|---|
| CN | 104044239 A | 9/2014 |
| DE | 10 2007 058 105 A1 | 6/2009 |

(Continued)

OTHER PUBLICATIONS

Second Chinese Office Action in CN 201780086396.8, dated Jun. 10, 2021.
(Continued)

*Primary Examiner* — Mathieu D Vargot
(74) *Attorney, Agent, or Firm* — Collard & Roe, P.C.

(57) ABSTRACT

In a method for the manufacture of a transmissive optical system from a blank, material ablation is achieved on the blank with an ablative laser, and the pulse duration of the ablative laser is less than 1 ns, and preferably lies between 3 fs and 100 fs, or between 100 fs and 10 ps.

18 Claims, 5 Drawing Sheets

(51) Int. Cl.
*B23K 26/36* (2014.01)
*B23K 26/082* (2014.01)
*B23K 26/352* (2014.01)
*A61F 2/16* (2006.01)
*B23K 26/03* (2006.01)
*B23K 26/402* (2014.01)
*B29C 45/00* (2006.01)
*B29C 45/16* (2006.01)
*B29C 45/77* (2006.01)
*B29D 11/02* (2006.01)
*G02C 7/06* (2006.01)
*B22F 10/66* (2021.01)
*B33Y 80/00* (2015.01)
*B29K 33/04* (2006.01)
*B29L 11/00* (2006.01)
*B22F 10/20* (2021.01)

(52) U.S. Cl.
CPC ........ *B23K 26/0624* (2015.10); *B23K 26/082* (2015.10); *B23K 26/3576* (2018.08); *B23K 26/402* (2013.01); *B29C 45/0055* (2013.01); *B29C 45/16* (2013.01); *B29C 45/77* (2013.01); *B29D 11/00451* (2013.01); *B29D 11/00951* (2013.01); *B29D 11/023* (2013.01); *G02C 7/06* (2013.01); *A61F 2240/002* (2013.01); *B22F 10/20* (2021.01); *B29C 2945/76498* (2013.01); *B29K 2033/04* (2013.01); *B29K 2995/0018* (2013.01); *B29L 2011/0008* (2013.01); *B29L 2011/0016* (2013.01); *B33Y 80/00* (2014.12)

(58) Field of Classification Search
CPC  B23K 26/3576; B23K 26/034; B23K 26/402; B29C 45/0055; B29C 45/16; A61F 2/1618; G02C 7/06
See application file for complete search history.

(56) References Cited

U.S. PATENT DOCUMENTS

| | | | |
|---|---|---|---|
| RE36,872 E * | 9/2000 | Zair | B23K 26/073 606/11 |
| 6,215,096 B1 | 4/2001 | Von Wallfeld et al. | |
| 10,203,521 B2 | 2/2019 | Pugh et al. | |
| 2005/0155956 A1* | 7/2005 | Hamada | B23K 26/40 219/121.68 |
| 2006/0192310 A1* | 8/2006 | Lindacher | B29D 11/00125 264/1.32 |
| 2006/0228897 A1* | 10/2006 | Timans | H01L 21/67115 438/758 |
| 2009/0168014 A1* | 7/2009 | Rooney | B29D 11/00125 351/159.73 |
| 2015/0146162 A1 | 5/2015 | Pugh et al. | |
| 2015/0167926 A1 | 6/2015 | Yu | |
| 2018/0169791 A1* | 6/2018 | Miller | B23K 26/3576 |

FOREIGN PATENT DOCUMENTS

| | | |
|---|---|---|
| EP | 0 954 255 B1 | 7/2002 |
| WO | 96/31315 A1 | 10/1996 |
| WO | 2004/026566 A1 | 4/2004 |
| WO | WO 2004/090612 * | 10/2004 |
| WO | 2012/119761 A1 | 9/2012 |
| WO | 2015/165435 A1 | 11/2015 |

OTHER PUBLICATIONS

Zheng Zhiren et al., Optics, CPEL1951505P, Oct. 31, 2015, pp. 265-272, Category A, See Second Chinese Office Action for relevance.

International Search Report in PCT/DE2017/000337, dated Mar. 16, 2018.

* cited by examiner

METHOD FOR PRODUCING A TRANSMISSIVE OPTICS

CROSS REFERENCE TO RELATED APPLICATIONS

This application is the National Stage of PCT/DE2017/000337 filed on Oct. 12, 2017, which claims priority under 35 U.S.C. § 119 of German Application Nos. 10 2016 014 747.4 filed on Dec. 13, 2016 and 10 2017 002 986.5 filed on Mar. 28, 2017, the disclosures of which are incorporated by reference. The international application under PCT article 21(2) was not published in English.

BACKGROUND OF THE INVENTION

1. Field of the Invention

The invention concerns a method for the manufacture of a transmissive optical system from a blank. Here the transmissive optical system is usually a lens. The invention concerns in particular the manufacture of an intraocular lens, a contact lens, a refractive implant, or a spectacle lens. The invention also concerns the processing of optical surfaces, which are partially mirrored and partially translucent to radiation.

2. Description of the Related Art

WO 96/31315 describes the treatment of arbitrary 3D-form surfaces by means of a laser. In particular, this involves the manufacture of precise sealing surfaces on molding tools.

WO 2012/119761 A1 concerns a method for the production of optical elements by means of processing with energetic radiation, preferably with laser radiation. In this method, blanks of quartz glass are first treated by coarse ablation and subsequently by polishing and fine ablation. This iterative method with a plurality of steps is particularly suitable for hard materials such as glass or steel.

DE 10 2007 058 105 A1 describes a method for the manufacture of a transmissive optical system with an ablative laser. In this method, however, material ablation is not achieved with the laser on a blank, but with an ablative medium that is supplied separately by an evaporator onto the surface to be processed. In this method, the material ablation is achieved with the ablative medium, and the laser acts not on the surface of the blank, but rather on the ablative medium, which, as a vaporous phase or in a condensed liquid phase, absorbs the laser radiation between the laser and the blank. The pulse durations of less than 500 fs specified in this application relate to the laser radiation impinging on the vaporous or liquid ablative medium, and not to a laser beam that leads to material ablation on the blank. Such methods are suitable for particularly hard materials.

U.S. Pat. No. 5,143,660 A describes an injection molding process for the manufacture of plastic lenses. Here special holes are formed in the lens, which serve to accommodate liquids, in particular such as medicaments.

The invention therefore has as its object the presentation of a generic method that can also be used for blanks made of softer materials. In particular, the method should enable rapid, cost-effective manufacture.

SUMMARY OF THE INVENTION

This object is achieved by a method with the features according to the invention. Advantageous developments are discussed below.

The extremely short pulse duration of the ablative laser has the consequence that the material of the blank that evaporates during the pulse does not hinder the energy input after the vaporization, and that after each pulse, within the short interruption between two pulses, the vapor can also largely escape from the processing zone, or the laser can be directed onto another processing zone. This enables a precise surface finish, in which small craters located very close to one another can be created on the surface of the blank.

The short pulse duration has the consequence that virtually no interaction occurs between the melt or material of the blank vaporizing under the laser radiation. The material ablation is achieved by direct vaporization and thus the treated material is hardly damaged. The ultra-short laser pulses with durations ranging from a few femtoseconds to a few picoseconds or nanoseconds enable new processing methods that are not possible with conventional tools. These laser flashes lead to extremely high peak intensities, which can be achieved with relatively low pulse energies by virtue of the strong temporal compression. This enables highly precise material ablation and the processing of materials sensitive to temperature.

It is advantageous if the blank is manufactured from plastic. Monomers and polymers, and also combinations of these, and in particular transparent plastics, are suitable for this purpose.

The blank particularly preferably comprises an acrylate. At the same time the blank can also be manufactured from diverse plastics. The acrylate is preferably transparent or partially transparent. Acrylates with or without plasticisers can be used. Suitable materials are, for example, HI56 SPECS®, PMMA, CI26® or Contaflex CI18®, hydrogel, silicone, or combinations of a collagen and a polymer, such as Collamer®.

The blank can be cut from, or out of, a base body, such as, in particular, a cylindrical rod or a plate. It is particularly advantageous if the blank is manufactured by means of injection molding or extrusion.

A particularly advantageous variant of embodiment envisages that the blank is manufactured from a powder-form, liquid or gaseous material by means of additive production (3D-printing). Here the blank can already have a three-dimensional shape matched to the final shape, which can also be of an asymmetric design. Both the build-up method, and also a combination with the described ablation method, can be applied here.

An advantageous variant of embodiment envisages that a blank is used that has a density gradient. Such a density gradient leads to a locally diverse optical refractive behavior within the blank. The result is that by adjusting the optical density within the blank, a blank can be manufactured and used, which, with a lower surface curvature, effects the same light refraction as a homogeneous blank.

Alternatively or cumulatively, it is proposed that the blank be made of different materials or types of material. This results in a multi-material blank, which leads to a particular refractive behavior by virtue of the material selection and the local arrangement of material. A density gradient can also be achieved as a result of a particular selection of materials with diverse densities, which determines the refractive behaviour of the blank and the optical system.

If, for example, the outer shell regions of a cylinder have an optical density that differs from that of the core region, radiation incident on the plane face of the cylinder is deflected in accordance with the optical density of the material, without the surface having to be of a curved design. Thus in the case of a circular lens the density gradient in the radial direction enables a reduction of the curvature of the surface. This has the consequence that the processing of the less curved surface with a laser beam is facilitated, since as a result of the lower curvature, the laser beam can more easily be guided approximately at right angles to a normal on the curvature of the surface. However, the blank can already have a refractive behavior that is close to the desired target shape of the lens. By this means the processing effort on the lens is reduced.

Therefore, it is further proposed that a blank with a circular cross-section is used, which has an optical density towards the center that differs from that towards the edge.

A density gradient on the lens enables the lens to be manufactured with less curvature, or even with no curvature. This leads to a lens that can be manufactured such that it is flexible and can be rolled up. By this means it is possible to fold up or roll up a lens such that it is very small, and can be inserted into the eye through a particularly small opening. Thus, a very small incision in the cornea is sufficient to remove the old destructible lens, and to insert a new lens into the eye, which then only unfolds or rolls out in the eye.

The statements regarding the different materials and the density gradient are each essential to the invention per se, also independently of the pulse duration specified in accordance with the invention.

It is advantageous if the pulse energy is varied during the ablation and/or polishing. Thus, it is proposed that the energy of the laser be varied over time. This makes it possible to ablate or polish certain surface regions with a higher pulse energy than in other surface regions. If, for example, the laser beam is guided along a meandering line over the surface of the blank, the energy input can be reduced in the turning regions, for example.

If the ablation of matter is the primary mechanism for altering the shape of the blank, reference is made to an ablative process, or an ablative laser. If, on the other hand, the shape is to remain unaltered, and the surface is only to be smoothed, reference is made to a polishing process, or a polishing laser.

It is particularly advantageous if the shape of the processed optical system in the region of the processed surface is measured after each laser pulse. Either the total ablation per surface region can be determined, or the actual crater shape can be determined. Optical coherence tomography preferably serves this purpose. This enables the location data to be stored, and for this data to be taken into account in subsequent processing of the surface, or processing of an adjacent surface. The measurement is carried out either immediately after a pulse, or in the time until processing of the measured surface is repeated, or until the processing of an adjacent surface. This enables a precision in the micron range, or even in the sub-micron range.

In addition to the measurement of the processed surface, it is advantageous if, during processing, the process temperature is monitored with a measuring system, preferably with a pyrometer or a thermal camera. This also makes it possible to control the process temperature so as to keep it within a defined bandwidth.

The laser pulse usually has a Gaussian distribution of intensity over the surface. However, a particular precision is achieved in the processing of surfaces if the pulse energy distribution of a pulse is locally asymmetric. In a deviation from a rectangular pulse, the edges of the rectangle can thus be formed differently. In particular, on one side the pulse can rise more sharply towards the center than it falls away from the center on the other side. This allows the energy distribution over the surface of the laser beam to be varied, such that when the beam hits a curved surface, a vaporization is achieved that is matched to the curved surface. In particular, the depth of the crater created by the laser pulse can also be reduced, without reducing the volume vaporized during the pulse.

This enables an almost constant ablation over the surface that is to be treated. In addition, the ablation profile can be varied and manipulated as required.

Moreover, the crater depth should be essentially constant over the entire surface that is to be processed. Essentially, this has the consequence that the intensity distribution of the laser beam is adjusted such that, for example, when irradiating a circular region with a radius r, the average crater depth on a circular region with a radius r/2 is at most twice as deep as the average crater depth in an annular region in the region r/2 to r. The deviation is preferably even in the sub-µm range.

One form of embodiment envisages that the pulse energy distribution during a pulse on a circular or an oval surface has at least one maximum in the radial direction. The intensity distribution of the pulse can, for example, be represented as the shape of a volcanic crater, so that a higher intensity acts in the edge regions of the circular oval surface than in the central region. This makes it possible, depending on the task, to vary the intensity distribution of the pulse over the surface impinged upon by the pulse in an individual manner. This pulse shape can be set once, or can be altered during the processing. It is therefore proposed that the pulse energy distribution be varied transverse to the direction of irradiation during the processing.

The statements regarding the local and temporal energy distributions are each essential to the invention per se, also independently of the pulse duration specified in accordance with the invention.

The effect of a laser beam varies, depending on whether the laser beam impinges onto the surface to be processed at right angles, or at another angle. As a result, the alignment of the laser beam relative to the processed surface also influences the ablation result. In order to limit these differences, it is proposed that during the processing of a curved optical system, the alignment of the laser beam is maintained essentially at right angles to a tangent plane at the intersection of the laser beam and the optical system. Here "essentially" means with a deviation of less than 40% and preferably less than 10%. Since "at right angles" describes an angle of the laser beam of 90° to the tangent plane, "essentially at right angles" describes, for example, an angle of the laser beam to the tangent plane of greater than 70°. Alternatively or cumulatively, the intensity or the intensity distribution of the laser beam can also be varied as a function of the angle of incidence.

In order to ensure that the laser beam impinges onto the surface to be processed as far as possible at right angles, the beam can be deflected via mirrors. However, the positions of the laser and the optical system to be processed can also be altered relative to each other. It is therefore proposed that the position and/or the alignment of the blank or the laser be moved during processing.

The processing effort can be greatly reduced by using a blank that already has a defined shape on one side or a plurality of sides, such as, in particular, a convex or concave shape, and is only processed with the laser on one side. A preferred variant of embodiment envisages that the blank is to be symmetrically formed on one side, and on another side is to be processed asymmetrically, or in a free-form manner.

The statements regarding the alignment of the laser beam and the shape of the blank are each essential to the invention per se, also independently of the pulse duration specified in accordance with the invention.

The precise processing of optical systems makes it possible to produce a visual aid, such as an intraocular lens or a contact lens, for a patient in an individual manner. For this it is proposed that an eye of a patient is first measured, and that thereby a data set is created, and that the ablative laser and/or the polishing laser is subsequently controlled on the basis of the data of this data set.

The eye can be measured by means of biometry and/or topometry so as to determine the axial length of the eyeball, the anterior corneal surface, the posterior corneal surface, the corneal thickness, and/or the refractive index of the cornea. Topometry allows the peripheral corneal radii to be measured with an ophthalmometer or keratometer, in addition to the central radii, in order to obtain meaningful surface parameters, for example, for the customization of contact lenses or intraocular lenses. Topometry provides individual measured values, from which the surface character can be approximated, and keratography delivers a complete surface profile. This results in a data set for the target shape, which enables the individual manufacture of a lens or other visual aid. The visual defects can originate from all elements of the eye. A measurement of the individual elements or the use of ray tracing to determine the diffraction of a radiation beam passing through an eye makes it possible to define a visual correction in order to compensate for these errors with a visual correction medium.

It is advantageous if a data set is already created in the course of measurement, which can easily be converted into a computer control program for the production of a lens.

Various individually manufactured visual aids or vision correction aids can be used, or standard visual aids can be combined with individually manufactured vision correction aids. However, it is also possible to replace just the lens with a corrected intraocular lens, in order to correct as many of the errors of the eye as possible.

Such a method has been described in EP 0 954 255 B1. It has been proposed that an artificial lens should be cut with a laser. This method is not economically feasible, because it is time-consuming to cut a lens with a laser such that it corresponds exactly to a specific target shape, and is so smooth that no unwanted refractions of light occur. Only the combination of the method with a plastic material such as, in particular, an acrylate, and a plastic-vaporizing laser, has led to an economical method. This method is essential to the invention, also independently of the above-cited method steps, in particular as a two-stage method, with an ablative laser used for material ablation, and a polishing laser used for a polishing operation.

Here the lens can also have multi-focal functions. Moreover, the lens can be used to correct errors caused by scattering in the eye, such as that caused, in particular, by age-related scattering centers in the vitreous humor. In addition, reflections in the eye, local absorption, alterations in polarization in the eye, and individual visual impairments, can be corrected such that the quality of the correction attains or even exceeds the optical resolution of the retina (retina quality IOL).

Furthermore, it is proposed to alter systematically the optical density of the surface of the optical system, by ablation and/or polishing, such that the altered refractive index prevents reflections. In particular, extreme polishing can minimise light refractions, such as the Fabry-Pérot effect, and multiple reflections. The polish then acts like an anti-reflection coating. In particular this can be achieved by altering the refractive index in different layers.

In particular, to eliminate scattered radiation and to be able to manufacture lenses with an increased depth of field and multi-focal IOLs, it is proposed to modify the material of the blank with the laser radiation such that the finished lens has an optical density gradient. An alteration of the density gradient can be achieved by ablative and additive methods. For example, a density gradient can be achieved by a radially co-rotated orientation of the laser light spot or the laser focus. In particular, a density gradient can also be achieved by means of a defined beam distribution. Thus, processing can take place with a higher intensity of the laser beam in a radially inner region than in a radially outer region in order to achieve a density gradient or regions of different density. Correspondingly, processing can also take place with a lower intensity of the laser beam in a radially inner region than in a radially outer region in order to achieve a density gradient or regions of different density. This gradient or density difference can be taken into account when calculating the refraction behavior of a transmissive optical system. An optical density difference between two regions of the lens of at least 0.01 is advantageous, allowing any, preferably radially symmetrical, refractive index gradient to be generated as a step change in density, or as a continuous density transition.

A particularly important field of application for this method is therefore the manufacture of the optical system of an intraocular lens.

Technically, it has proved to be advantageous if the ablative laser is operated such that it effects a material ablation of 0.01 to 10 µm per pulse, and preferably of 0.02 µm to 5 µm per pulse, and particularly preferably of 0.02 µm to 0.5 µm per pulse. Depending on the required material ablation, the ablation can also be carried out in a plurality of layers, whereby the ablation per layer should be less than 20 µm, preferably less than 2 µm, and particularly preferably less than 1 µm. At first it is possible to work with the ablation of a larger amount of material, and when approaching the target shape the ablation per layer can be reduced. The result is that firstly greater ablation is effected with greater intensities or also larger irradiated regions, and subsequently a smaller ablation per pulse is effected, so that the surface becomes as smooth as possible, and requires less polishing.

It has been shown that it is advantageous if the ablative laser is operated with a laser wavelength of 100 to 1,200 nm, and preferably less than 400 nm, such as in particular between 193 nm and 370 nm. Preferred wavelengths are 193, 248, 266, 343 and 355 nm.

During the ablation, the focal diameter of the ablative laser should be between 5 and 50 µm, and preferably approx. 20 µm.

The scanning rate of the ablative laser lies between 100 and 5,000 mm/s, and preferably between 500 and 5,000 mm/s, and particularly preferably at approx. 1,000 mm/s.

The pulse energy of the ablative laser can lie between 0.1 µJ and 10 µJ, and preferably at approx. 1 µJ.

The repetition rate of the ablative laser can lie between 5 kHz and 5,000 kHz, and preferably between 50 and 200, or between 10 and 500 kHz.

An advantageous variant of the method envisages that the laser beam of the ablative laser firstly removes material at some distance from the target shape, until at least 50% of the material has been removed, and only then is material removed in a region closer to the target shape. Here the laser can be guided upwards and downwards. With guidance of the laser upward, only one element is firstly ablated radially on the very outside, and then, as a rule, a smaller element, reaching further radially inwards. "Downwards" means that firstly a large element is ablated radially from the outside as far as the final shape, and then a smaller element is ablated underneath.

Moreover, it has proved to be advantageous if the distance between the ablation craters created by the individual laser pulses on the surface within one ablation layer is not constant. This distance can also be varied so as to adjust the mean ablated layer density. By this means the ablation per surface is altered by the distance between the pulse footprints on the optical system that is to be processed. Closely spaced pulse footprints result in greater ablation, while widely spaced pulse footprints result in less ablation.

For polishing, it is proposed that the polishing laser be operated in a pulsed or modulated manner with a pulse duration of more than 1 µs. By this means an optimum polishing of, for example, plastics, can be achieved.

Preferred laser wavelengths for the polishing process lie in the range between 0.1 µm and 100 µm, and preferably between 9 µm and 11 µm, or between 0.1 µm and 0.4 µm, or between 1 and 12 µm.

A particular form of method management envisages that the polishing laser is operated continuously. The laser is therefore not pulsed during the polishing process, but rather the beam is moved relative to the surface of the optical system, preferably with a varying intensity. In contrast to a pulsed laser, in this case a particular laser power is always present.

For the polishing process, it has proved to be advantageous if the polishing laser has a beam diameter at the workpiece of less than 10 mm, and preferably of between 0.1 mm and 8 mm. The polishing process can be simplified, in that the polishing laser has a beam diameter at the workpiece that is greater than or equal to that of the surface to be polished. By this means it is possible to polish the said surface all at once, without moving the laser backwards and forwards over the surface.

An advantageous feed rate of the polishing laser lies between 1 and 100 mm/s.

Furthermore, it is advantageous if the polishing laser is formed into a "quasi-line" by means of a scanning movement with a scanning rate of 500 mm/s to 20,000 mm/s. By moving the laser beam backwards and forwards, even a pulsed laser does not produce individual craters, but rather a deepened surface or a groove.

The polishing laser can be operated with an average laser power of 1 to 500 W, preferably of approx. 100 to 300 W. It is advantageous if less than 30, and preferably only 1 to 10, passes are carried out with the polishing laser in order to polish the optical system.

The polishing laser can also be operated with a line length that is at least as long as an extent of the surface to be polished. The laser beam is thus guided as a line over the surface to be polished, and at the same time care is taken to ensure that the entire surface is covered by the laser beam.

The object underlying the invention is also achieved by a lens, which has a density in one region that is 1% lower than in another region of the lens. Such a density gradient leads to a particular refractive behavior, whereby the lens causes a different refraction of light not only by virtue of its shape, but also, and in particular, by virtue of its density in diverse regions. It is advantageous if the difference is between 2 and 5% or even higher, such as, for example, more than 10%.

It is furthermore advantageous if the lens has a surface region and a core region, and the density in the surface region is higher than in the core region. Cumulatively or alternatively, the lens can have a circular cross-section and a radial density gradient.

Depending on the application, it can be advantageous if the lens reflects less than 5%, and preferably less than 1%, of the incident radiation.

The statements regarding the parameters of the laser in the course of ablation and polishing are each essential to the invention per se, also independently of the pulse duration specified in accordance with the invention and the other features cited above.

BRIEF DESCRIPTION OF THE DRAWINGS

Inventive examples of embodiment are illustrated in the figures and are described in what follows. Here.

DETAILED DESCRIPTION OF THE PREFERRED EMBODIMENTS

Figure 1:
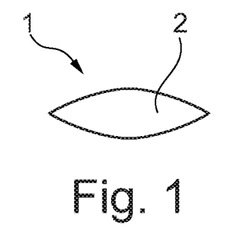
FIG. 1 shows schematically a blank for the manufacture of a lens.
Figure 2:
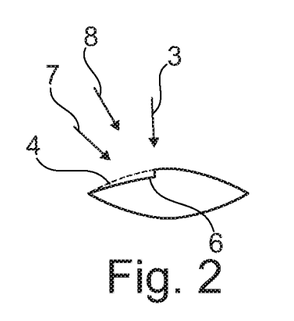
FIG. 2 shows schematically the blank during the laser processing.

FIG. 1 shows a lens blank 2 as a transmissive optical system 1. FIG. 2 shows how this blank 2 is processed by means of an ablative laser 3. In the example shown in FIG. 2, the indicated material ablation 4 has already been achieved on the left-hand side of the lens 2 with the laser 3. After the material has been ablated, the measuring device 5 measures the shape 6 of the lens 2 in the region of the processed surface. On the basis of the measured values, this makes it possible to adjust the type of pulse of the laser 3, preferably whilst still in the course of processing. In addition, the process temperature is already monitored during the processing with the pyrometer 7. The process temperature can also be influenced and, if required, can even be controlled, by adjustment of the nature of the laser beam of the laser 3.

Figure 3:
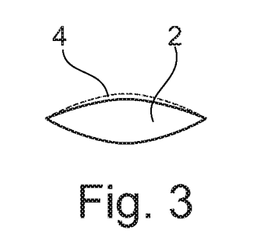
FIG. 3 shows schematically the processed blank after the laser processing.

After ablation, the blank 2 has the shape shown in FIG. 3, with a reduced volume that is to be attributed to the material ablation 4.

Figure 4:
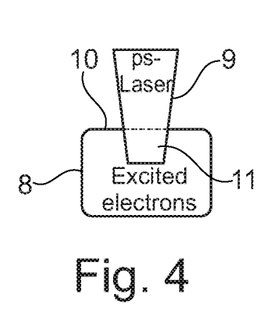
FIG. 4 shows schematically the impingement of a laser beam onto a lens surface.
Figure 5:
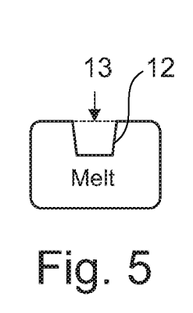
FIG. 5 shows schematically the melt and the vapor generated after the laser beam impinges onto the surface.

The blank is a plastic and in the present case is an acrylate 8. The said blank can also comprise other materials, such as other plastics, or glass. However, the surface of the blank to be reworked is made of plastic. FIG. 4 shows how the laser beam 9 impinges onto the surface 10 of the acrylate 8, and thereby penetrates into the acrylate in the shape of a cup in the region 11. The pulse duration of the ablative laser is about 100 femtoseconds and the acrylate is thereby vaporized in the region 11. This creates a cup-shaped region 12 of an acrylate melt, and, within this cup-shaped region 12, a region 13 of vapor.

Figure 6:
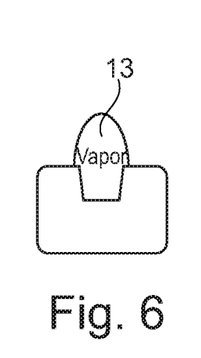
FIG. 6 shows schematically the evaporation of the generated vapor.

FIG. 6 shows how the melt 12 solidifies again and the vapor 13 evaporates. Thus, at the end of the process, the crater 14 shown in FIG. 7 remains in the acrylate region 8.

Figure 7:
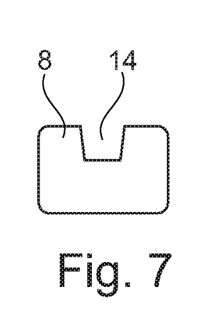
FIG. 7 shows schematically a crater created on the lens surface.

By the arrangement of a plurality of craters of this type in close proximity to each other, a planar material ablation 4 is achieved. The resulting surface structure is rough as a result of the linking together of the craters. By minimizing the depth of the crater, and minimizing the distances between the craters, the roughness of the plastic surface can be reduced.

Figure 8:
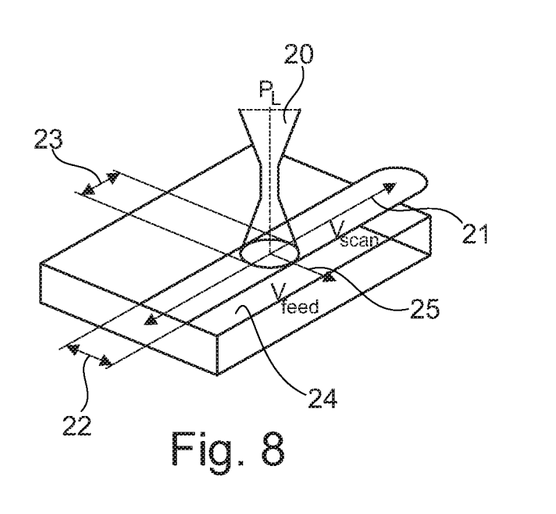
FIG. 8 shows schematically the smoothing of a lens surface with a laser beam.

It is advantageous for the smoothing of the surface if the laser intensity is minimised, and/or the footprint of the laser on the surface to be processed is increased, so that material is only melted, and, as far as possible, no material evaporates. A polishing laser 20 is usually used for this purpose, which is scanned along the line 21 with a scanning rate ($V_{scan}$) and a footprint width 22, 23 over the surface 24. The polishing laser 20 is moved forward at a feed rate ($V_{feed}$) in the direction of the arrow 25, at right angles to the line 21.

Figure 9:
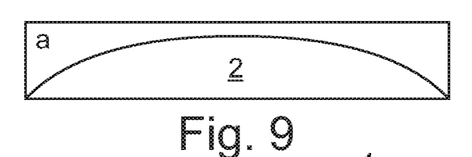
FIG. 9 shows schematically the surface of an untreated lens blank.
Figure 10:
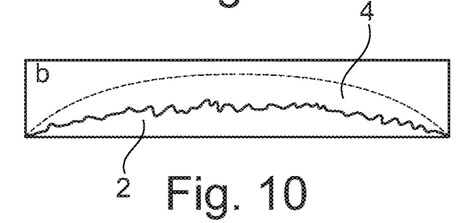
FIG. 10 shows schematically the lens surface after laser ablation.
Figure 11:
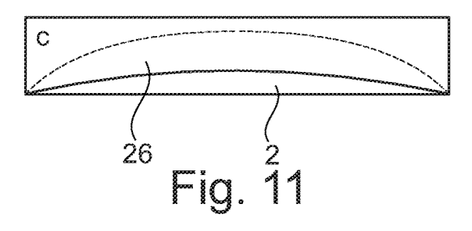
FIG. 11 shows schematically the lens surface after polishing.

As a consequence, as shown in FIGS. 9 to 11, the blank 2 is first processed with the ablative laser to achieve material ablation 4, resulting in a rough surface of the blank 2. The subsequent laser polishing produces the smooth surface 26 of the blank 2 shown in FIG. 11.

In the example of embodiment, the material surface shown in FIG. 10 is created by selective material ablation of an intraocular lens 2 from the initial shape shown in FIG. 9, and the said material surface is then smoothed by laser polishing until it is transparent. This creates the material surface shown in FIG. 11.

During material ablation 4 with the ablative laser 3, care is taken to ensure that systematically localised material ablation is achieved by the action of ultra-short pulses of laser radiation of about 100 or 200 femtoseconds only at the point of impingement of the laser onto the surface, without any thermal damage to the surrounding material. In the example of embodiment, a laser wavelength of 343 nm is used, so that the laser radiation is absorbed near the surface as a result of the small optical penetration depth of this laser wavelength in the acrylate.

By comparing the initial shape and the target shape of the surface, the required ablation depth and thus the required number of laser pulses at each point on the surface are determined. In this manner the material ablation 4 can be determined by the number of laser pulses per unit surface area without altering the nature of the laser radiation. Here the laser beam 30 can be guided in a meandering manner over the surface to be processed, in particular for the laser material ablation. On the basis of the calculated number of laser pulses per unit surface area, the laser is switched on and off during its passage over the surface to be processed.

Figure 12:
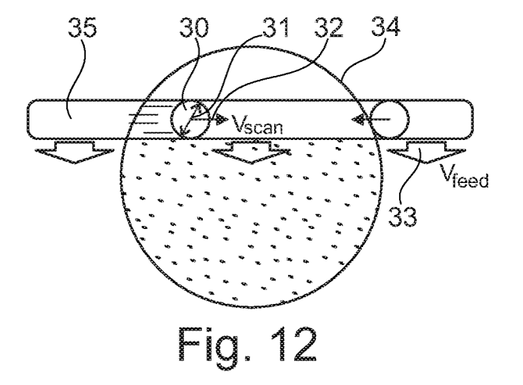
FIG. 12 shows schematically the feed of a laser during processing.

In the example of embodiment shown in FIG. 12, a beam diameter 31 of the laser radiation on the material surface of approx. 20 μm, a repetition rate of 100 kHz, and a scanning rate 32 of 1,000 mm/s are used. This results in a feed rate 33 ($V_{feed}$), with which the laser 30 is guided over the lens 34.

For the subsequent laser polishing, a laser with a wavelength of 10.6 μm is used, since this wavelength is also absorbed near the surface in the material. The laser is operated continuously and the laser power is in the range of 50 to 100 watts. As a consequence the material surface is melted by the action of the laser radiation during laser polishing, and is then smoothed by the surface tension before it solidifies once again.

In the example of embodiment shown in FIG. 12, 20 iterations (the number of passes) are carried out, so as to polish the surface gradually, whereby each iteration reduces the surface roughness until the target roughness is achieved. A pause of 20 seconds is envisaged between the iterations to prevent the sample from overheating.

The processing strategy for the iteration shown in FIG. 12 is characterised by the use of a bi-directional scanning strategy, with a scanning rate of 5,000 mm/s, thereby creating a quasi-line focus. The said quasi-line focus 35 is guided with the feed rate 33 of 30 to 40 mm/s over the surface of the lens 34 to be polished. In this example of embodiment, the beam diameter 31 at the workpiece is 6 mm. Temperature control is preferably also used so as to improve the stability of the laser polishing further.

Figure 13:
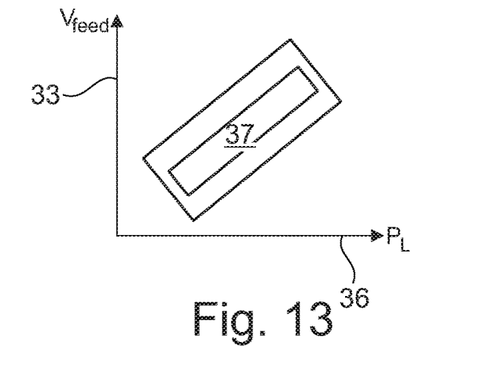
FIG. 13 shows schematically the dependence of the feed rate on the laser power.

With a higher average laser power a higher feed rate is to be used, and with a lower average laser power the feed rate is reduced. This process can therefore be scaled. The dependence between feed rate 33 and average laser power 36 is shown in FIG. 13. This results in the hatched preferred working region 37.

Figure 14:
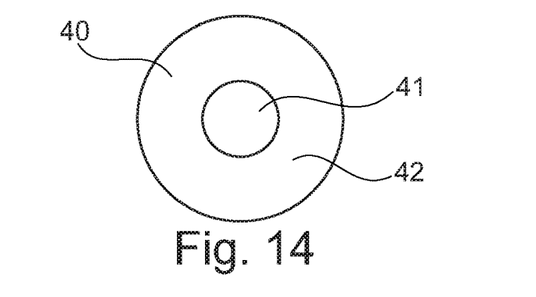
FIG. 14 shows schematically a plan view onto a lens with a density gradient.

FIG. 14 shows a particular blank 40 that is manufactured by injection molding. As a consequence of the injection molding method this blank has a density gradient. Here the central region 41 is formed with a higher density than the edge region 42. This density gradient can be generated in injection molding by the pressure conditions during the injection process, or also by a multi-component injection molding process in which different plastics are used. In particular, in the case of additive production from a powder-form, liquid or gaseous material, a blank can easily be manufactured with a density gradient or from different materials. This density gradient leads to a particular refraction of the light by the lens 40. In order that the different densities of the blank 40 do not impair the process of material ablation and polishing, a region with a different density can also be provided in the interior of the lens 40, while the surface to be processed with the surface region relevant to the processing has a uniform density.

Figure 16:
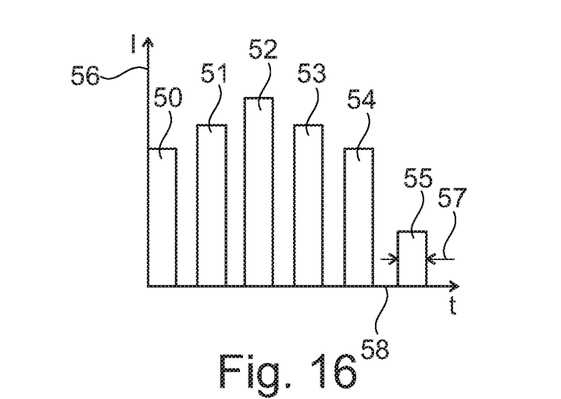
FIG. 16 shows schematically the variation of pulse intensity over time.

It is advantageous if the pulse energy is varied during ablation and/or polishing. To this end FIG. 16 shows the intensity of different pulses 50 to 55, which follow each other in time and have different intensities 56, but the same pulse durations 57 (only numbered in an exemplary manner). Thus the intensity 56 of the pulses 50 to 55 varies over time 58. Correspondingly, the pulse duration 57 of the individual pulses 50 to 55 can also vary, while the pulse intensity remains constant. Finally, both the intensity 56 and the pulse duration 57 can be varied and preferably controlled over time, in order to influence the ablation or polishing process in an optimal manner, and in order to achieve rapid processing without overheating.

Figure 17:
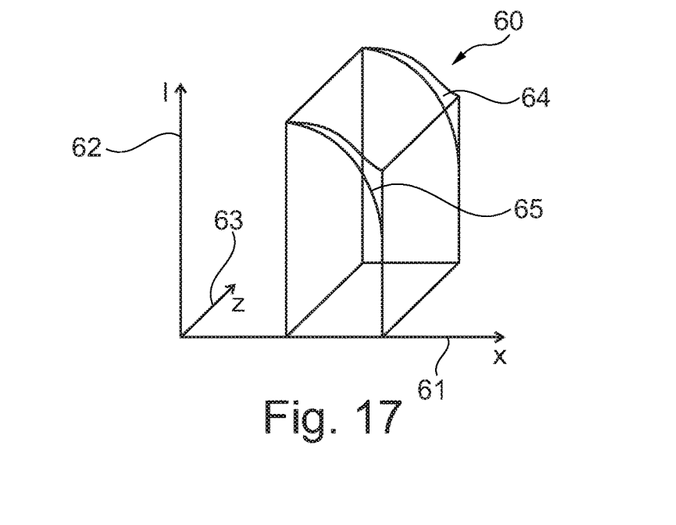
FIG. 17 shows schematically the local variation of pulse intensity.

The local intensity distribution of a pulse 60 on the spatial axes 61 and 63 is shown in an exemplary manner in FIG. 17. This pulse shows a locally bounded higher pulse energy 62 on the left-hand side than on the right-hand side. For example, the pulse can drop slowly along the surface 64, or rapidly along the curved surface 65, so that the right-hand side of the pulse has a significantly lower energy concentration than its left-hand side. This makes it possible, for example, to vary the radiation intensity applied to a surface region over time as a laser beam moves over a surface.

Figure 18:
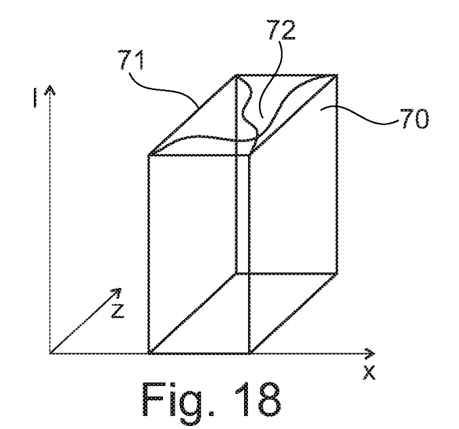
FIG. 18 shows schematically a pulse with a central intensity sink.

FIG. 18 shows a particular local energy distribution of a pulse 70, in which a higher energy is present in the edge region 71 of the pulse 70 than in the central region 72. When the pulse impinges onto the surface of a lens this results in a higher energy being applied to the edge region of the resulting crater than to the central region of the crater. The crater is therefore given less of a cup shape and more of a rectangular shape, so that a plurality of craters placed side-by-side form an approximately planar surface.

In order to optimise this effect, it is proposed that the pulse energy distribution be varied transverse to the direction of radiation during processing.

Figure 19:
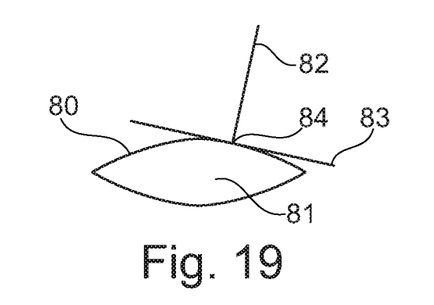
FIG. 19 shows schematically the alignment of the laser beam relative to the lens.

In order to achieve homogeneous processing of a lenticular surface 80 of a lens 81, it is advantageous if the laser beam 82 is maintained essentially at right angles to a tangent 83 at the point of intersection 84 of the laser beam 82 and the lens 81. This can be achieved by varying the alignment of the laser beam during processing and maintaining the position of the lens 81 constant, or by altering the alignment of the lens 81 relative to the laser beam 82 by moving the lens 81 during processing. Needless to say, both the lens and laser can be moved so as to align the laser beam 82 as nearly at right angles as possible to the normal 83 on the surface of the lens. Moreover, instead of moving the laser, the laser beam can also be aligned with the aid of a mirror so that it impinges onto the lens surface as nearly at right angles as possible.

Figure 15:
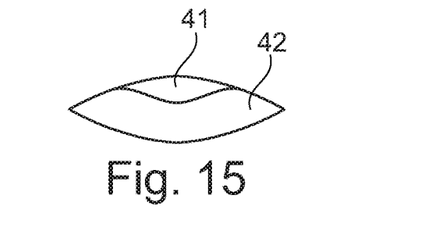
FIG. 15 shows schematically a section through the lens shown in FIG. 14.
Figure 20:
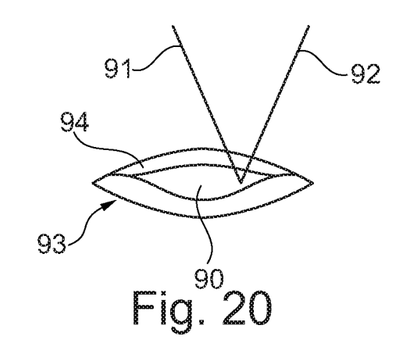
FIG. 20 shows schematically the laser processing in the interior of the lens.

As in the example of the lens shown in FIGS. 14 and 15, the density of the lens can be varied by the choice of material or by the material processing of the blank. However, the density can also be altered during processing by material ablation and/or polishing. This makes it possible to provide, by the nature of the laser beam, densities on the lens surface that differ in terms of gradient and are locally bounded. The density on the material surface can be increased such that reflections are prevented by the altered refractive index. However, the density can also be altered with the laser beam, or by means of a plurality of laser beams 91, 92, in the interior 90 of a lens 93 such that the refraction of the finished lens does not result from the surface shape of the lens, but rather from a density gradient in the surface region 94 of the lens 93 and/or in the interior region 90 of the lens 93.

Figure 21:
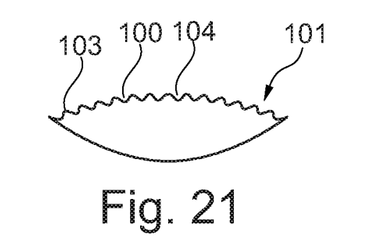
FIG. 21 shows schematically ablation craters with different spatial separations on the lens surface.

The arrangement of the ablation craters 100 on the surface 101 of a lens 102 is shown in FIG. 21. Here the craters 100 are spaced further apart in the edge region 103 than in the central region 104. This is just one example to show how the nature of the processing of the surface can be varied by means of the number of craters per unit surface area.

Figure 22:
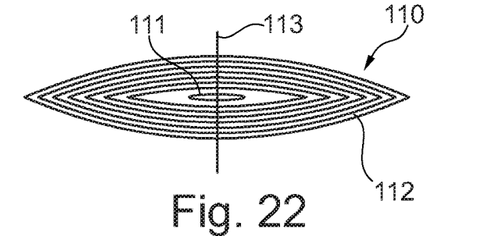
FIG. 22 shows schematically a lens with an increased density in the interior of the lens.

The lens 110 shown in FIG. 22 has a central region 111, which has a greater density than the radially outer region 112.

Figure 23:
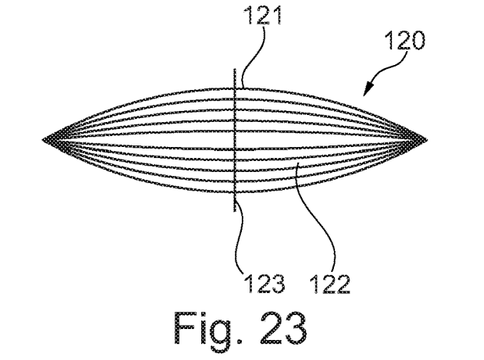
FIG. 23 shows schematically a lens with an increased density at the surface of the lens.

The inverted density distribution was implemented with the lens 120 shown in FIG. 23. There an outer region is illustrated as graphically darker so as to indicate the higher density, while the interior region 122 is illustrated as brighter so as to indicate the lower density.

Figure 24:
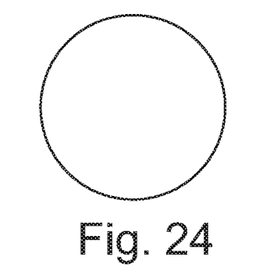
FIG. 24 shows schematically a plan view onto the lens shown in FIG. 23.

In the plan view shown in FIG. 24, a uniform density can be discerned, if just the visible surface is considered. In both examples of embodiment a density gradient is therefore present in the direction of the optical axis 113 or 123.

Figure 25:
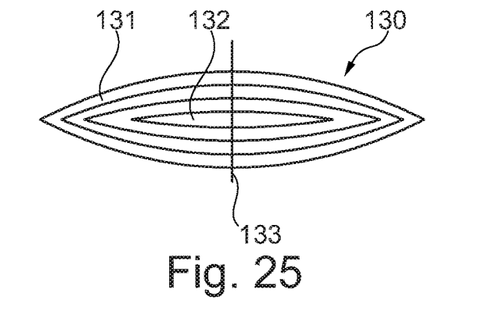
FIG. 25 shows schematically a lens with an increased density in the radially outer region of the lens.
Figure 26:
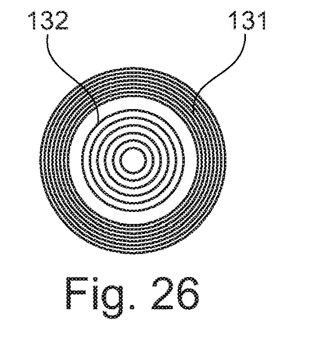
FIG. 26 shows schematically a plan view onto the lens shown in FIG. 25.

FIG. 25 shows a lens 130 with a radial density gradient. In the region of the optical axis 133, there is a region 132 with a lower density than in the radially outer region 131. The plan view in FIG. 26 therefore shows a darker radially outer region 131 and a brighter central region 132 with a lower density.

Figure 27:
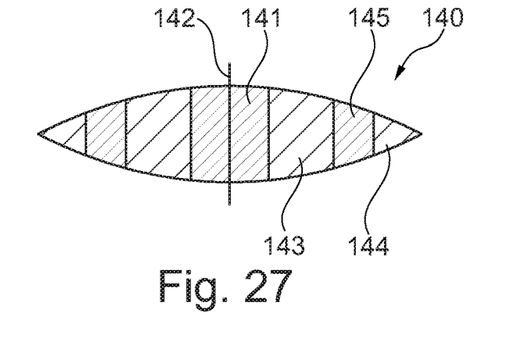
FIG. 27 shows schematically a lens with a density altering in the radial direction and FIG. 28 shows schematically a plan view onto the lens shown in FIG. 27.

FIG. 27 shows a lens 140 with a multi-focal density gradient. Here, regions 143 and 144 with a lower optical density alternate outwards in the radial direction from a central region 141 on the optical axis 142; between these there is a region 145 with a higher optical density.

Figure 28:
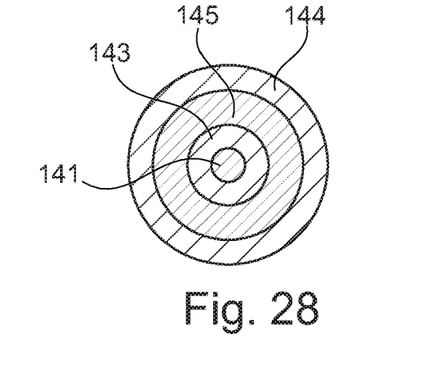

FIG. 28 shows in a plan view that the regions of higher and lower optical density are annular in form.

In all the examples of embodiment shown, the optical density can migrate via a gradient into an altered optical density, and, alternatively, regions of different optical densities can lie clearly bounded next to each other. Here the varying optical density can be used to influence the refractive behavior of the lens when a light beam passes through it, and its deflection. Alternatively or cumulatively, the reflection properties, especially at the boundary surface of the lens surface, can be influenced by way of its density and the hardness that usually accompanies the latter.

The invention claimed is:

1. A method for the manufacture of a transmissive optical system from a plastic blank,
   wherein material ablation is achieved on the blank with an ablative plastic-vaporizing laser,
   wherein the focal diameter of the ablative laser lies between 5 µm and 50 µm;
   wherein the pulse duration of the ablative laser is less than 1 ns and the pulse energy, which corresponds to the ablation thickness per pulse, lies between 0.1 µJ and 10 µJ and varies in time depending on the position of the blank,
   wherein the pulse energy is changed by changing the pulse power or the pulse duration,
   wherein the ablative laser effects a material ablation of 0.01 to 10 µm per pulse.

2. The method in accordance with claim 1, wherein the blank, initially treated with the ablative laser, is further processed with a polishing laser having a beam diameter at the blank of between 0.1 mm and 8 mm.

3. The method in accordance with claim 1, wherein the blank has a circular cross-section and an optical density towards the center that differs from that towards the edge.

4. The method in accordance with claim 1, wherein during processing, the process temperature is monitored and/or controlled with a pyrometer.

5. The method in accordance with claim 1, wherein the blank is symmetrically formed on one side, and on another side is processed asymmetrically or in a free-form manner.

6. The method in accordance with claim 1, wherein an eye of a patient is first measured and a data set is thereby generated, and the ablative laser and/or the polishing laser is subsequently controlled on the basis of the data of this data set.

7. The method in accordance with claim 1, wherein with the laser radiation the material of the blank is altered such that the finished lens has an optical density gradient.

8. The method in accordance with claim 1, wherein the optical system is an intraocular lens.

9. The method in accordance with claim 1, wherein the ablative laser is operated such that it effects a material ablation of 0.02 µm to 5 µm.

10. The method in accordance with claim 1, wherein the ablative laser is operated with a laser wavelength of less than 400 nm.

11. The method in accordance with claim 1, wherein the focal diameter of the ablative laser lies between 20 µm and 50 µm.

12. The method in accordance with claim 1, wherein the scanning rate of the ablative laser lies between 500 and 5,000 mm/s.

13. The method in accordance with claim 1, wherein the repetition rate of the ablative laser lies between 5 kHz and 5,000 kHz.

14. The method in accordance with claim 1, wherein the polishing laser is operated with a laser wavelength between 1 and 12 µm.

15. The method in accordance with claim 1, wherein the polishing laser is operated continuously.

16. The method in accordance with claim 1, wherein a beam of the polishing laser is formed into a line by means of a scanning movement, with a scanning rate of 500 mm/s to 20,000 mm/s.

17. The method in accordance with claim 1, wherein with the polishing laser less than 30 passes are carried out.

18. The method in accordance with claim 1, wherein an ablation profile is created that is arbitrarily manipulated or varied from individual patient data by varying the pulse energy perpendicular to the beam direction of propagation.

* * * * *

UNITED STATES PATENT AND TRADEMARK OFFICE
CERTIFICATE OF CORRECTION

PATENT NO. : 11,786,994 B2
APPLICATION NO. : 16/468397
DATED : October 17, 2023
INVENTOR(S) : Axel Von Wallfeld et al.

Page 1 of 1

It is certified that error appears in the above-identified patent and that said Letters Patent is hereby corrected as shown below:

In the Claims

In Claim 14, Line 1 (Column 14, Line 7): please change "1" to --2--

In Claim 15, Line 1 (Column 14, Line 10): please change "1" to --2--

In Claim 16, Line 1 (Column 14, Line 12): please change "1" to --2--

In Claim 17, Line 1 (Column 14, Line 16): please change "1" to --2--

Signed and Sealed this
Twenty-eighth Day of November, 2023

Katherine Kelly Vidal
*Director of the United States Patent and Trademark Office*